(12) United States Patent
Liao et al.

(10) Patent No.: US 8,494,245 B2
(45) Date of Patent: Jul. 23, 2013

(54) SYSTEM AND METHOD FOR GUIDING TRANSCATHETER AORTIC VALVE IMPLANTATIONS BASED ON INTERVENTIONAL C-ARM CT IMAGING

(75) Inventors: Rui Liao, Princeton Junction, NJ (US); Yefeng Zheng, Dayton, NJ (US); Matthias John, Nürnberg (DE); Alois Nöttling, Pottenstein (DE); Jan Boese, Eckental (DE); Uwe Kirschstein, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 452 days.

(21) Appl. No.: 12/945,045

(22) Filed: Nov. 12, 2010

(65) Prior Publication Data
US 2011/0222750 A1 Sep. 15, 2011

Related U.S. Application Data

(60) Provisional application No. 61/311,923, filed on Mar. 9, 2010.

(51) Int. Cl.
*G06K 9/00* (2006.01)
(52) U.S. Cl.
USPC ........... 382/131; 345/419; 345/420; 345/424; 600/407
(58) Field of Classification Search
USPC ............ 382/131; 345/419, 420, 424; 600/407
See application file for complete search history.

(56) References Cited

U.S. PATENT DOCUMENTS

| 8,009,887 | B2 * | 8/2011 | Ionasec et al. | 382/128 |
|---|---|---|---|---|
| 2008/0262814 | A1 * | 10/2008 | Zheng et al. | 703/11 |
| 2009/0123050 | A1 * | 5/2009 | Ionasec et al. | 382/131 |
| 2010/0036239 | A1 * | 2/2010 | Klingenbeck-Regn | 600/425 |
| 2010/0239148 | A1 * | 9/2010 | Zheng et al. | 382/131 |
| 2011/0052026 | A1 * | 3/2011 | Liao et al. | 382/131 |
| 2011/0096969 | A1 * | 4/2011 | Zheng et al. | 382/131 |
| 2011/0164035 | A1 * | 7/2011 | Liao et al. | 345/419 |
| 2011/0249794 | A1 * | 10/2011 | Florent et al. | 378/62 |

OTHER PUBLICATIONS

Gessat et al., "A Planning System for Transapical Aortic Valve Implantation", Mar. 13, 2009, Proc. of SPIE vol. 7261, 72611E-72611E-12.*
Ionasec et al., "Dynamic Model-Driven Quantitative and Visual Evaluation of the Aortic Valve from 4D CT", 2008, Springer-Verlag, MICCAI 2008, Part I, LNCS 5241, pp. 686-694.*
Leipsic et al., "The Evolving Role of MDCT in Transcatheter Aortic Valve Replacement: A Radiologists' Perspective", Sep. 2009, American Journal of Roentgenology, vol. 193, No. 3, W214-W219.*
Walther et al., "Transapical approach for sutureless stent-fixed aortic valve implantation: experimental results", 2006, European Journal of Cardio-thoracic Surgery 29, 703-708.*

* cited by examiner

*Primary Examiner* — Jason M Repko
*Assistant Examiner* — Katrina Fujita

(57) ABSTRACT

A method for guiding transcatheter aortic valve implantations includes receiving an interventional 3D image of an aortic root reconstructed from a sequence of 2D images acquired from a C-arm computed tomography (CT) system being rotated about a patient through a predetermined number of degrees, segmenting the aortic root and detecting aortic root landmarks in the 3D image, where the aortic root landmarks include three lowest points of aortic root cusps, two coronary artery ostia, and three commissures points where the cusps meet, cropping an area inside the segmented aortic root out of the 3D volume for volume rendering, centering the 3D image on an intersection of two orthogonal planes, each containing the two detected coronary ostia, that are orthogonal to a plane spanned by three lowest points of the aortic root cusps, and volume rendering the 3D cropped aortic root image together with the detected landmarks onto a 2D image.

32 Claims, 4 Drawing Sheets

SYSTEM AND METHOD FOR GUIDING TRANSCATHETER AORTIC VALVE IMPLANTATIONS BASED ON INTERVENTIONAL C-ARM CT IMAGING

CROSS REFERENCE TO RELATED UNITED STATES APPLICATIONS

This application claims priority from "System to Guide Transcatheter Aortic Valve Implantations Based on Interventional C-Arm CT Imaging", U.S. Provisional Application No. 61/311,923 of Liao, et al., filed Mar. 9, 2010, the contents of which are herein incorporated by reference in their entirety.

TECHNICAL FIELD

This disclosure is directed to methods for guiding aortic valve replacements using real-time digital imaging.

DISCUSSION OF THE RELATED ART

Transcatheter aortic valve implantation (TAVI) is a hybrid operating-room procedure that is performed in high risk patients with aortic valve defects and is considered to be an alternative to conventional open heart surgical techniques that need sternotomy with extracorporeal circulation and cardioplegic cardiac arrest. Aortic valve disease is the most common valvular disease in developed countries. Implantation of a prosthetic aortic valve is often necessary to replace the severely damaged native valve. Though open-chest valve surgery is a well established procedure, minimally invasive TAVI is an emerging technique, especially for high-risk patients, to minimize the surgical trauma. Before the surgery, several important parameters of the aortic valve need to be extracted for surgery planning. Recently, C-arm CT emerges as a new imaging technique with the following advantages, compared to conventional CT. Since both the 3D volume and 2D fluoroscopic images are captured on the same device within a short time interval, overlay of the 3D patient-specific aorta model onto a 2D image is straightforward and accurate (except patient motion). Besides providing visual guidance, the extracted aortic root can predict the best C-arm angulation (the optimal orientation of the imaging plane) to mitigate the foreshortening effect.

A fully automatic system of aorta segmentation and valve landmark detection can pay a key role in seamlessly integrating C-arm CT into the TAVI workflow. During a TAVI procedure, a bio-prosthesis is positioned and deployed via a catheter into the aortic root of the patient. A transapical AVI uses an antegrade access in which the catheter and the prosthesis are inserted via small incisions in the chest and the apex of the left ventricle. During transfemoral AVI, a retrograde insertion of the catheter is performed via the femoral artery and the aortic arch. The minimal-invasive TAVI approach requires the use of X-ray angiography and fluoroscopy imaging to guide the procedure, and therefore these procedures are usually performed in operating rooms equipped with an angiography C-arm system. To render the anatomy of the aortic root visible under X-ray imaging, a contrast agent is injected. Due to renal insufficiencies in many of these patients, it is important to minimize the amount of the contrast agent.

FIGS. 1(a)-(c) illustrate a typical transapical aortic valve implantation under X-ray guidance. FIG. 1(a) depicts an angiographic C-arm system 10 able to acquire interventional 3D images. FIG. 1(b) depicts contrast injection via a pigtail catheter 11 immediately prior to valve deployment. FIG. 1(c) depicts the implanted valve 12.

Prior to performing a TAVI, it is important to angulate the C-arm with respect to the aortic root anatomy of the patient. Rotational symmetric prostheses require an angulation perpendicular to the aortic root to be placed correctly. Prostheses that model the leaflet anatomy of the aortic root require an angulation that can outline the commissures, that is, the connection of the valvular leaflets. An appropriate angulation can be achieved with iterated C-arm angulations, each followed by an angiogram using approximately 15 ml contrast agent per injection to double-check the reached position. Further angiograms are needed for correct prosthesis positioning and for functional control after implant.

FIGS. 2(a)-(c) are images acquired during a TAVI procedure. FIG. 2(a) shows an image from the rotational acquisition scene acquired under rapid pacing and contrast injection into the aortic root 21. FIG. 2(b) is a C-arm CT image reconstructed from this scene. FIG. 2(c) depicts a segmented aortic root with landmarks, including the commissures 22, the lowest points of the cusps 23, and the coronary ostia 24.

SUMMARY OF THE INVENTION

Exemplary embodiments of the invention as described herein generally include methods and systems for performing 3D C-arm CT imaging during transcatheter aortic valve implantations. A system according to an embodiment of the invention can make the use of interventional 3D imaging for transcatheter aortic valve implantations feasible and valuable, by providing image guidance based on interventional C-arm CT images to add detailed 3D information to the procedure. A system according to an embodiment of the invention may be set up and used by a physician in the complex environment of an operating room during a TAVI, and is sufficiently fast to minimize the user interaction and to allow table-side control. A system according to an embodiment of the invention can be used in parallel to conventional fluoroscopy and angiography. It supports the physician in measuring critical anatomical parameters, finding an optimum C-arm angulation, guiding the positioning and deployment of the prosthesis by 3D overlay upon the fluoroscopic images, and may be fully integrated into an existing angiography C-arm system, and designed to minimize the necessary user interaction, because aortic root segmentation, landmark detection and optimal visualization are made fully automatic. A system according to an embodiment of the invention provides for the interactive adjustment of an optimal angulation requiring only low doses of contrast agent, measured information about critical coronary ostia distances, and additional anatomical orientation by the fluoroscopic overlay when implanting the prostheses. A system and method according to an embodiment of the invention was evaluated for 20 clinical cases.

According to an aspect of the invention, there is provided a method for guiding transcatheter aortic valve implantations, including receiving an interventional 3D image of an aortic root reconstructed from a sequence of 2D images acquired from a C-arm computed tomography (CT) system being rotated about a patient through a predetermined number of degrees, segmenting the aortic root and detecting aortic root landmarks in the 3D image, where the aortic root landmarks include three lowest points of aortic root cusps, two coronary artery ostia, and three commissures points where the cusps meet, cropping an area inside the segmented aortic root out of the 3D volume for volume rendering, centering the 3D image on an intersection of two orthogonal planes, each containing the two detected coronary ostia, that are orthogonal to a plane spanned by three lowest points of the aortic root cusps, and volume rendering the 3D cropped aortic root image together with the detected landmarks onto a 2D image.

According to a further aspect of the invention, the method includes displaying the 2D volume rendering together with three orthogonal multi-planar reformatted (MPR) intersection planes.

According to a further aspect of the invention, segmenting the aortic root and detecting aortic root landmarks in the 3D image comprises estimating a position, orientation, and scale of the aortic root to estimate a pose of the aortic root, calculating a mean aortic root shape from a training set, aligning the mean aortic root shape with the estimated pose of the aortic root, refining a boundary of the aortic root using a learning-based 3D boundary detector.

According to a further aspect of the invention, a hierarchical approach is used that first detects a global object having all eight valve landmarks, uses the position, orientation, and scale of this global object to infer the rough position of individual landmarks, and refines each landmark in a small region under the guidance of its own specific landmark detector.

According to a further aspect of the invention, the hierarchical approach comprises a marginal space learning (MSL) algorithm.

According to a further aspect of the invention, the method includes dilating the cropped aortic root shape, and adding a ball shape around each detected coronary ostia when cropping the aortic root shape from the 3D image.

According to a further aspect of the invention, the method includes calculating parameters for optimal values of a window center and a window width for a volume rendering transfer function by calculating $$c_{opt} = f_{c,in} \times m_{in} + f_{c,out} \times m_{out} + c_{offset},$$

$$w_{opt} = f_{w,in} \times m_{in} + f_{w,out} \times m_{out} + w_{offset},$$

where $m_{out}$ is the mean intensity of all voxels outside the boundary of the segmented aortic root with a distance less than n voxels to the boundary, $m_{in}$ is the mean intensity of all voxels inside the boundary of the segmented aortic root with a distance less than n voxels to the boundary, $f_{c,in}$ is a coefficient for $m_{in}$ for the optimal value of the window center, $f_{c,out}$ is a coefficient for $m_{out}$ for the optimal value of the window center, $f_{w,in}$ is a coefficient for $m_{in}$ for the optimal value of the window width, and $f_{w,out}$ is a coefficient for $m_{out}$ for the optimal value of the window width.

According to a further aspect of the invention, the method includes manually adjusting the optimal window width and window center values for the transfer function window for each of a set of training images, associating a definition of $c_{opt}$ and $w_{opt}$ with each training image, determining a value of $m_{in}$ and $m_{out}$ for each training image, and solving for the parameters $f_{c,in}$, $f_{c,out}$, $f_{w,in}$, $f_{w,out}$ in the set of equations using a least squares fit.

According to a further aspect of the invention, the method includes applying dilation and erosion operators on a binary segmentation mask of the aortic root to isolate those voxels within a predetermined distance from the aortic root boundary, where only those voxels outside and inside the aortic root boundary that are found by the dilation and erosion operations are used to calculate the optimized transfer function window parameters.

According to a further aspect of the invention, landmarks in the volume rendering window are rendered on top of the volume, the perpendicularity circle is displayed in the 3D volume window and the ruler is displayed in one of the intersection planes.

According to a further aspect of the invention, the intersection planes are shown as maximum intensity projections (MIP) with a small thickness.

According to a further aspect of the invention, the method includes overlaying the volume rendering on a 2D live fluoroscopic image to display the cropped aortic root volume together with the detected landmarks, and presenting a contour view of the aortic root that displays information needed for a prosthesis positioning and deployment.

According to a further aspect of the invention, rendering the contour includes segmenting the volume rendered aortic root image by thresholding the image intensity, where border voxels are detected as those having at least one neighboring voxel that belongs to a background, calculating gradients of foreground voxels are calculated, and assigning gradients of the border voxels a maximum value, to create a gradient map, detecting edge voxels on the gradient map by a hysteresis thresholding step, with a low and high threshold determined as a given percentage of the gradient map, and pruning the detected edge voxels by removing connected components whose size is smaller than a predetermined number of voxels.

According to a further aspect of the invention, the method includes deriving a perpendicularity circle parallel to a plane spanned by three lowest points of the aortic root cusps and a ruler orthogonal to that plane, where the perpendicularity circle is displayed in the 3D volume rendering, and the ruler is displayed in one of the intersection planes.

According to a another aspect of the invention, there is provided a program storage device readable by a computer, tangibly embodying a program of instructions executable by the computer to perform the method steps for guiding transcatheter aortic valve implantations.

According to a another aspect of the invention, there is provided a method for guiding transcatheter aortic valve implantations, including receiving an interventional 3D image of an aortic root reconstructed from a sequence of 2D images acquired from a C-aim computed tomography (CT) system being rotated about a patient through a predetermined number of degrees, segmenting the aortic root and detecting aortic root landmarks in the 3D image, where the aortic root landmarks include three lowest points of aortic root cusps, two coronary artery ostia, and three commissures points where the cusps meet, calculating parameters for optimal values of a window center and a window width for a volume rendering transfer function by calculating $$c_{opt} = f_{c,in} \times m_{in} + f_{c,out} \times m_{out} + c_{offset},$$

$$w_{opt} = f_{w,in} \times m_{in} + f_{w,out} \times m_{out} + w_{offset},$$

where $m_{out}$ is the mean intensity of all voxels outside the boundary of the segmented aortic root with a distance less than n voxels to the boundary, $m_{in}$ is the mean intensity of all voxels inside the boundary of the segmented aortic root with a distance less than n voxels to the boundary, $f_{c,in}$ is a coefficient for $m_{in}$ for the optimal value of the window center, $f_{out}$ is a coefficient for $m_{out}$ for the optimal value of the window center, $f_{w,in}$ is a coefficient for $m_{in}$ for the optimal value of the window width, and $f_{w,out}$ is a coefficient for $m_{out}$ for the optimal value of the window width, volume rendering the 3D cropped aortic root image together with the detected landmarks onto a 2D image, and overlaying the volume rendering on a 2D live fluoroscopic image to display the cropped aortic root volume together with the detected landmarks, and presenting a contour view of the aortic root that displays information needed for a prosthesis positioning and deployment.

According to a further aspect of the invention, the method includes cropping an area inside the segmented aortic root out of the 3D volume for volume rendering, dilating the cropped aortic root shape, and adding a ball shape around each detected coronary ostia when cropping the aortic root shape from the 3D image.

According to a further aspect of the invention, the method includes centering the 3D image on an intersection of two orthogonal planes, each containing the two detected coronary ostia, that are orthogonal to a plane spanned by three lowest points of the aortic root cusps.

According to a further aspect of the invention, the method includes deriving a perpendicularity circle parallel to a plane spanned by three lowest points of the aortic root cusps and a ruler orthogonal to that plane, and displaying the 2D volume rendering together with three orthogonal multi-planar reformatted (MPR) intersection planes, where the perpendicularity circle is displayed in the 3D volume rendering, and the ruler is displayed in one of the intersection planes.

DETAILED DESCRIPTION OF EXEMPLARY EMBODIMENTS

Figure 1:
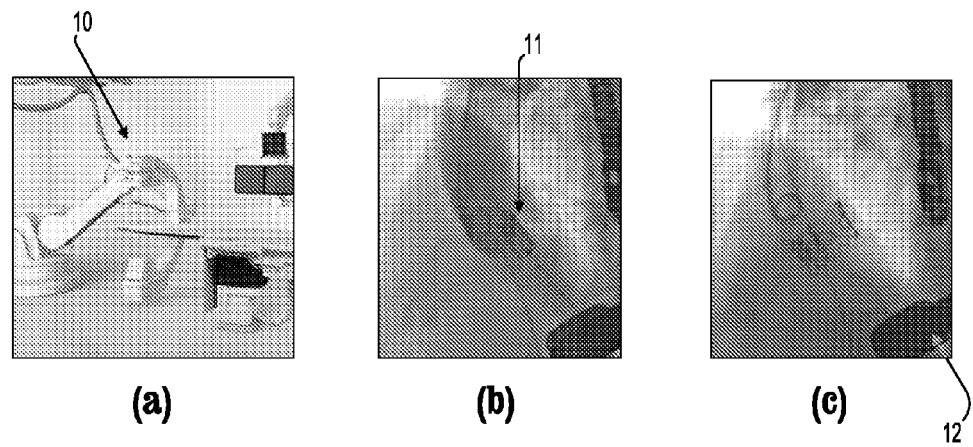
FIGS. 1(a)-(c) illustrate a typical transapical aortic valve implantation under X-ray guidance, according to an embodiment of the invention.
Figure 2:
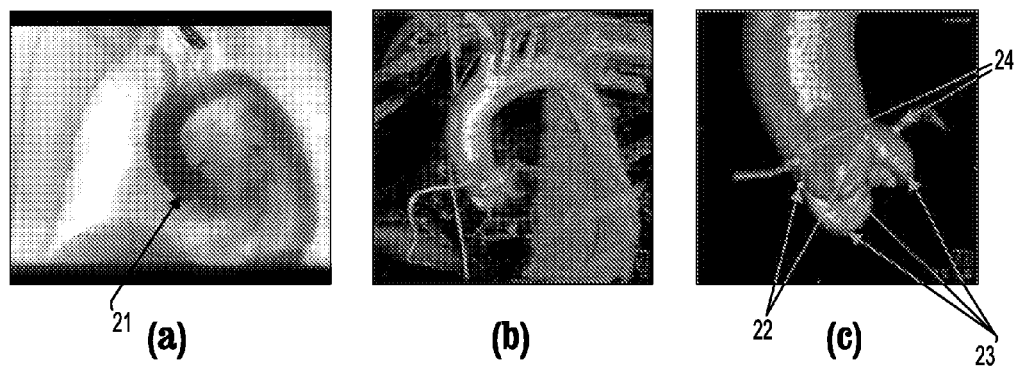
FIGS. 2(a)-(c) are images acquired during a TAVI procedure, according to an embodiment of the invention.

Exemplary embodiments of the invention as described herein generally include systems and methods for detecting acoustic shadows and evaluating image quality in 3D ultrasound images. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Prior to performing an implantation, the physician would obtain an interventional 3D image of the aortic root by acquiring a rotational 2D image sequence every 5 seconds over 220 degrees on the C-arm system. A contrast agent is injected over that time via a pigtail catheter into the aortic root. To compensate for motion artifacts, rapid ventricular heart pacing is applied, and patient breathing is stopped. Because of the rapid pacing, the blood flow is also minimized, which minimizes the amount of contrast agent needed.

Figure 3:
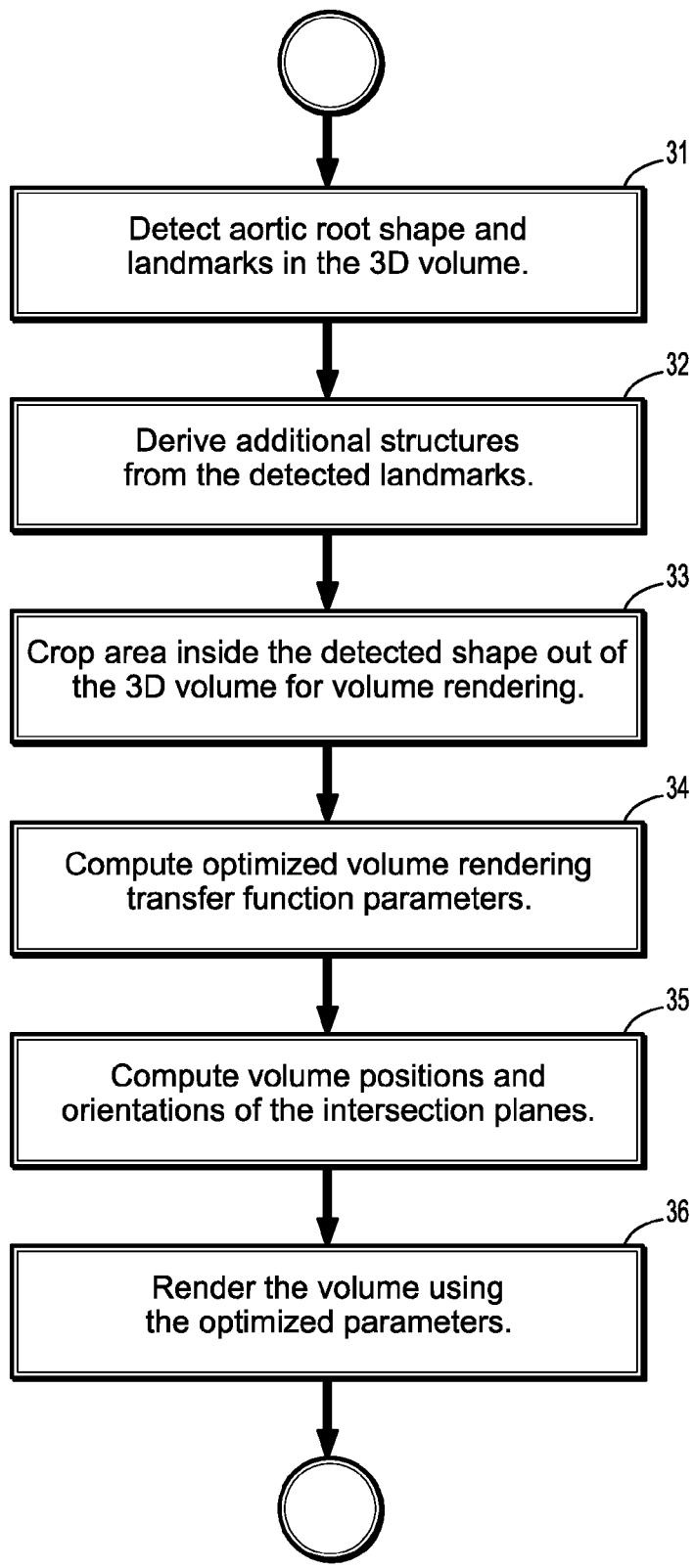
FIG. 3 is a flow chart of a method for guiding transcatheter aortic valve implantations based on interventional C-arm CT imaging, according to an embodiment of the invention.

After the 3D acquisition run is finished on the C-arm system, the 3D data is reconstructed, and the following steps, illustrated by the flow chart of FIG. 3, may be automatically performed.

Detecting Aortic Root Shape and Landmarks from the 3D Volume.

Referring now to the flowchart, a first step 31 is detecting the aortic root shape and landmarks in the 3D volume. A machine learning based algorithm may be used to detect the aortic root shape and some landmarks, in particular the lowest point of each aortic root cusps (to support finding a C-arm angulation perpendicular to the aortic root), the coronary artery ostia (which should stay open after prostheses implantation), the commissures points where the cusps meet (to help orienting anatomically designed valve prostheses), and finally the centerline.

First, one estimates the position, orientation, and scale of the aortic root. An exemplary, non-limiting algorithm for doing these estimations is the Marginal Space Learning algorithm. The mean aortic root shape, which is calculated from a training set, is then aligned with the estimated pose, followed by boundary refinement using a learning-based 3D boundary detector.

Marginal Space Learning (MSL) is used to solve the 9-dimensional similarity search problem for localizing the aortic root. MSL is more fully described in U.S. Patent Publication No. 2008/0101676, "System and Method For Segmenting Chambers Of A Heart In A Three Dimensional Image" of Zheng, et al., filed on Sep. 18, 2007, the contents of which are herein incorporated by reference in their entirety. Learned discriminative object models are used to exploit a large database of annotated 3D medical images. MSL reduces the number of testing hypotheses by about six orders of magnitude as will be described below. Steerable image features, which incorporate orientation and scale information into the distribution of sampling points, allow for the avoidance of time-consuming volume data rotation operations. After determining the similarity transformation of the aortic root, the 3D shape is estimated through learning-based boundary delineation.

In many instances, the posterior distribution or the object to be detected, such as the aortic root, is clustered in a small region in the high dimensional parameter space. It is not necessary to search the whole space uniformly and exhaustively. MSL incrementally learns classifiers on projected sample distributions, after which the dimensionality of the search space is gradually increased. As the dimensionality increases, the valid or positive space region becomes more restricted by previous marginal space classifiers. The localization is split into three steps: translation estimation, translation-orientation estimation, and full similarity estimation. After each step of the process, multiple candidates are maintained to increase the robustness of the results. Different features or learning methods can be used at each step. For example, in the translation estimation step rotation is treated as an intra-class variation so 3D Haar features can be used for detection. In the translation-orientation and similarity transformation estimation steps, steerable features are used.

After the similarity transformation estimation, an initial estimate of the non-rigid shape is obtained. Learning based 3D boundary detection is used to guide the shape deformation in the active shape model framework. Again, steerable features are used to train local detectors and find the boundary under any orientation, therefore avoiding time consuming volume rotation.

Steerable features have a very flexible framework in which a few points are sampled from the volume under a special pattern. A few points from the image are sampled under a special pattern. A few local features are extracted for each sampling point, such as voxel intensity and gradient. The sampling pattern can be used to test if a particular hypothesis is a good estimation of the similarity transformation of the object in the image. To evaluate the steerable features under a specified orientation, only the sampling pattern needs to be steered and no volume rotation is involved.

For each sampling point, a set of local features are extracted based on the intensity and the gradient. These features are used to train simple classifiers and a Probabilistic Boosting Tree (PBT) is used to combine the simple classifiers to get a strong classifier for the given parameters. The sampling pattern is steered, hence the name "steerable features". In the steerable feature framework, each feature is local, therefore efficient. The sampling pattern is global to capture the orientation and scale information. In this way, it combines the advantages of both global and local features.

A 3D object localization scheme using MSL and steerable features will now be described. First, the position of the object in the image is estimated. Given a set of candidates, they are split into two groups, positive and negative, based on their distance to the ground truth. The error in object position and scale estimation is not comparable with that of orientation estimation directly. Therefore, a normalized distance measure is defined using the searching step size.

$$E = \max_{i=1,\ldots,n} |V_i^l - V_i^t|/SearchStep_i \qquad (1)$$

where $V_i^l$ is the estimated value for dimension i and $V_i^t$ is the ground truth. A sample is regarded as a positive one if $E \leq 1.0$ and all the others are negative samples. The searching step for position estimation is one voxel, so a positive sample (X, Y, Z) should satisfy $$\max\{|X-X_t|,|Y-Y_t|,|Z-Z_t|\} \leq 1 \text{ voxel} \qquad (2)$$

where $(X_t, Y_t, Z_t)$ is the ground truth of the object center.

Given a set of positive and negative training samples, 3D Haar wavelet features are to extracted and a classifier is trained using the probabilistic boosting tree (PBT). Given a trained classifier, a training volume is scanned and a small number of candidates are preserved such that the solution is among top hypotheses.

Position-orientation and similarity transformation estimators are now trained. For a given volume, K candidates exist for the object position. The position and orientation are then estimated. The hypothesized parameter space is six dimensional so the dimension of the candidates needs to be augmented. For each candidate of the position, the orientation space is scanned uniformly to generate the hypotheses for orientation estimation. Orientation in 3D can be represented as three Euler angles, $\psi$, $\phi$, and $\theta$.

Each candidate $(X_i, Y_i, Z_i)$, is augmented with N hypotheses about orientation, $(X_i, Y_i, Z_i, \psi_j, \phi_j, \theta_j)$, j=1, ..., N. Some hypotheses are close to the ground truth (positive) and others are far away (negative). The learning goal is to distinguish the positive and negative samples using image features, i.e., steerable features. A hypothesis $(X, Y, Z, \psi, \phi, \theta)$ is regarded as a positive sample if it satisfies both EQ. (2) and $$\max\{|\psi-\psi_t|,|\phi-\phi_t|,|\theta-\theta_t|\} \leq 0.2 \qquad (3)$$

where $(\psi_t, \phi_t, \theta_t)$ represent the orientation ground truth. All the other hypotheses are regarded as negative samples.

A classifier is trained using PBT and steerable features. The trained classifier is used to prune the hypotheses to preserve only a few candidates.

The similarity estimation step in which scale is added is similar to the position-orientation transformation except learning is performed on the full nine dimensional similarity transformation space. The dimension of each candidate is augmented by scanning the scale subspace uniformly and exhaustively.

A testing procedure on an unseen volume will now be described. The input volume is first normalized to a uniform isotropic resolution, and all voxels are scanned using the trained position estimator. A predetermined number of top candidates $(X_i, Y_i, Z_i)$, i=1, ..., $K_1$ are kept. Each candidate is augmented with N hypotheses about orientation, $(X_i, Y_i, Z_i, \psi_j, \phi_j, \theta_j)$, j=1, ..., N. Next, the trained translation-orientation classifier is used to prune these $K_1 \times N$ hypotheses and the top $K_2$ candidates are retained, $(\hat{X}_i, \hat{Y}_i, \hat{Z}_i, \hat{\psi}_i, \hat{\phi}_i, \hat{\theta}_i)$, i=1, ..., $K_2$. Similarly, each candidate is augmented with M hypotheses about scaling and use the trained classifier to rank these $K_2 \times M$ hypotheses. The goal is to obtain a single estimate of the similarity transformation. In order to aggregate the multiple candidates, averaging of the top $K_3$ is performed. After the first stage, the position, orientation and scale of the object are obtained. The mean shape is aligned with the estimated transformation to obtain an estimate of the object shape. A set of local boundary detectors are trained using the steerable features with the regular sampling pattern. The boundary detectors are then used to move each landmark point to the optimal position where the estimated boundary probability is maximized. Shape constraint is enforced by projecting the adjusted shape onto a shape subspace to get the final result.

Besides detecting the aortic root, eight aortic valve landmarks are detected: three aortic hinge points, three aortic commissure points, and left and right coronary ostia since they are important in both surgery planning and providing visual guidance during surgery. The coronary ostia, i.e. the orifices of the coronary arteries, are situated within the two anterior sinuses, usually close to the sinutubular junction. Though it is possible to detect each landmark independently, the detection results may be geometrically inconsistent. According to an embodiment of the invention, a hierarchical approach may be used that first detects a global object comprised with all eight valve landmarks. This method is disclosed in Zheng, et al., "Automatic Aorta Segmentation and Valve Landmark Detection in C-Arm CT: Application to Aortic Valve Implantation", MICCAI 2010, Sep. 20-24, 2010, the contents of which are herein incorporated by reference in their entirety, as is summarized as follows. From the position, orientation, and scale of this global object, one can infer the rough position of individual landmarks. Each landmark is then refined in a small region, such as a cube of 20 mm centered on the initial position, under the guidance of its own specific landmark detector.

Similar to the aortic root detection, according to an embodiment of the invention, marginal space learning (MSL) may be used to efficiently detect the position, orientation, and scales of the global landmark object. For a learning based method, the ground truth of object pose is specified for each training volume, therefore, a learning algorithm can learn the implicit relationship to infer the correct pose from an unseen volume. A method according to an embodiment of the invention searches for an optimal shape which can represent the whole shape population accurately, therefore improving the initialization accuracy of the landmarks. Given a group of shapes, $M_1, M_2, \ldots, M_N$, an optimal shape $\overline{m}$ that represents the whole population minimizes the residual errors after alignment:

$$\overline{m} = \text{argmin}_m \sum_{i=1}^{N} \|T_i(m) - M_i\|^2. \quad (4)$$

The optimal shape $\overline{m}$ is referred to hereinbelow as the mean shape. $T_i$ is the corresponding transformation from the mean shape $\overline{m}$ to each individual shape $M_i$. This procedure is known as a generalized Procrustes analysis in statistical shape analysis.

Previously, the generalized Procrustes analysis has only been performed using a similarity transformation. However, an MSL according to an embodiment of the invention can estimate anisotropic scales quite efficiently. With more deformations compensated, the mean shape is a more accurate representation of the shape population. Therefore, according to an embodiment of the invention, T represents a combination of translation (T=[X, Y, Z]'), rotation (represented as a rotation matrix R), and anisotropic scaling ($S_x$, $S_y$, $S_z$). The anisotropic transformation of a 3D point P is $$T(P) = R \cdot \begin{bmatrix} S_x & 0 & 0 \\ 0 & S_y & 0 \\ 0 & 0 & S_z \end{bmatrix} \cdot P + T. \quad (5)$$

To the best of the inventor's knowledge, there are no closed-form solutions for estimating the anisotropic similarity transformation. According to an embodiment of the invention, an iterative algorithm is proposed. The similarity transformation (translation, rotation, and isotropic scaling) is estimated first, which has closed-form solutions. After compensating for the similarity transformation, the three anisotropic scaling parameters ($S_x$, $S_y$, $S_z$) are estimated, for which one can derive a closed-form solution. One can plug a routine for solving the anisotropic similarity transformation between two shapes, into the generalized Procrustes analysis method to search for the optimal mean shape $\overline{m}$. Besides the optimal mean shape, the transformation $T_i$ of the mean shape to each example shape $M_i$ is also calculated as a by-product, which provides the pose ground truth that MSL can learn to estimate.

Deriving Additional Structures from Detected Landmarks.

Next, at step 32, additional structures are derived from the detected landmarks. A circle is derived that is parallel to the plane spanned by the three lowest points of the cusps. Any three non-collinear points can define a unique circle that passes through all three points. This circumscribed circle can then be displaced by a predetermined distance below the plane of the three points along a direction normal to that plane. Visually, the circle degenerates into a straight line if and only if the three lowest points of the cusps are aligned, which corresponds to an optimal orthogonal angulation for prosthesis implantation. This circle is referred to herein below as the perpendicularity circle.

To estimate the coronary ostia positions, one can measure their distance to the plane through the three lowest cusp points. A ruler may be created that is orthogonal to that plane, which can make the measurement process transparent to the physician and can allow user compensation of the measurement in case of misdetected landmarks.

Cropping Area Inside Detected Shape Out of 3D Volume for Volume Rendering

At step 33, the area inside the detected shape is cropped out of the 3D volume for volume rendering. The segmented aortic root may be shown with volume visualization, rather than mesh visualization, for easier user verification of the landmark detection, since volume rendering can be performed on the original grey values of the image voxels.

A 100% correct aortic root detection is not guaranteed for all patients. Therefore, the extracted shape can be dilated by 2 mm for visualization purposes. So, if important structures are removed by the detection step, the user can visually detect parts of these structures.

Visualization of coronary arteries is useful because of challenges associated with automatically segmenting them. A ball shape can be added around each detected coronary ostia when cropping the aortic shape from the volume. An exemplary, non-limiting ball is about 15 mm in diameter. Thus, even if there are small errors in the detection of the coronary ostia, a segment of the corresponding coronary artery can be shown in a volume rendering.

Computing Optimized Volume Rendering Transfer Function Parameters

Optimized volume rendering transfer parameters are computed at step 34. Appropriate volume rendering parameters for the transfer function window center and transfer function window width may be automatically calculated based on the volume voxel values:

$$c_{opt} = f_{c,in} \times m_{in} + f_{c,out} \times m_{out} + c_{offset},$$

$$w_{opt} = f_{w,in} \times m_{in} + f_{w,out} \times m_{out} + w_{offset}. \quad (6)$$

Here, $m_{out}$ is the mean intensity of all the voxels outside the boundary of the segmented aortic root with a distance less than n pixels to the boundary, $m_{in}$ is the mean intensity of all the voxels inside the boundary of the segmented aortic root with a distance less than n pixels to the boundary, $f_{c,in}$ is the trained coefficient for $m_{in}$ for the optimal value of the window center, $f_{c,out}$ is the trained coefficient for $m_{out}$ for the optimal value of the window center, $f_{w,in}$ is the trained coefficient for $m_{in}$ for the optimal value of the window width, and $f_{w,out}$ is the trained coefficient for $m_{out}$ for the optimal value of the window width. An exemplary, non-limiting value of n is 3. $m_{out}$ ($m_{in}$) is a volume specific value and is determined by the mean intensities of all voxels outside (inside) the boundary of the segmented aortic root within a fixed distance to it.

To minimize the influence from peripheral structures and the inhomogeneities within the aorta due to, for example, contrast wash-out, only those voxels that are within a certain distance to the border of the segmented aorta are to be included in the final rendering. Thus, dilation and erosion are performed on the segmentation mask with a certain number of iterations to isolate those voxels within a certain distance to the aorta boundary. The number of iterations is determined by the distance threshold. An exemplary, non-limiting distance threshold is 3 voxels. The underlying set of voxels used for the subsequent transfers function window calculations are the bands of voxels outside and inside the aortic root boundary that are found by the dilation and erosion operations.

The six parameters of the weights and offsets in EQS. (6) are fixed values that can be obtained from a trained sample set of segmented volumes. For each of these training to volumes, the optimal window width and window center values for the transfer function window were manually adjusted. For each training image, $c_{opt}$ and $w_{opt}$ are obtained manually, and $m_{in}$ and $m_{out}$ are calculated automatically from its segmentation result. One set of EQS. (6) is then associated with each training image, to obtain an over-determined system of linear equations, and least square fitting can be used to solve the parameters of $f_{c,in}$, $f_{c,out}$, $f_{w,in}$, $f_{w,out}$ when multiple training images are available.

Computing Volume Positions and Orientations of Intersection Planes

At step 35, volume positions and orientations of intersection planes are computed. To provide a user with a good initial view to the volume, the volume is centered and zoomed based on two detected coronary ostia. To allow the user easy verification of the detected coronary ostia, two orthogonal volume intersection planes, both of which contain the two ostia, are shown. One of the planes is chosen to be orthogonal to the plane spanned by the three lowest points of the cusps. This plane contains the ruler discussed above and therefore allows the user to directly measure distances without manual user interactions.

Visualizing the 3D Volume and Intersection Planes

At step 36, according to the computations from the previous steps, the cropped aortic root volume together with the detected landmarks can be volume rendered using the optimized transfer function window parameters calculated in step 34. The 3D volume rendering can be displayed together with three orthogonal MPR intersection planes. The landmarks in the volume rendering window are rendered on top of the volume, which allows for easy identification of their positions even if the corresponding anatomy is hidden by the volume. The perpendicularity circle is displayed in the 3D volume window and the ruler is displayed in one of the intersection planes (also called MPR views). To allow for verification of the landmark detection, and to correct for cases in which the detection is slightly wrong, the intersection planes can be shown as maximum intensity projections (MIP) with a small thickness. An exemplary, non-limiting thickness is 15 mm.

Figure 4:
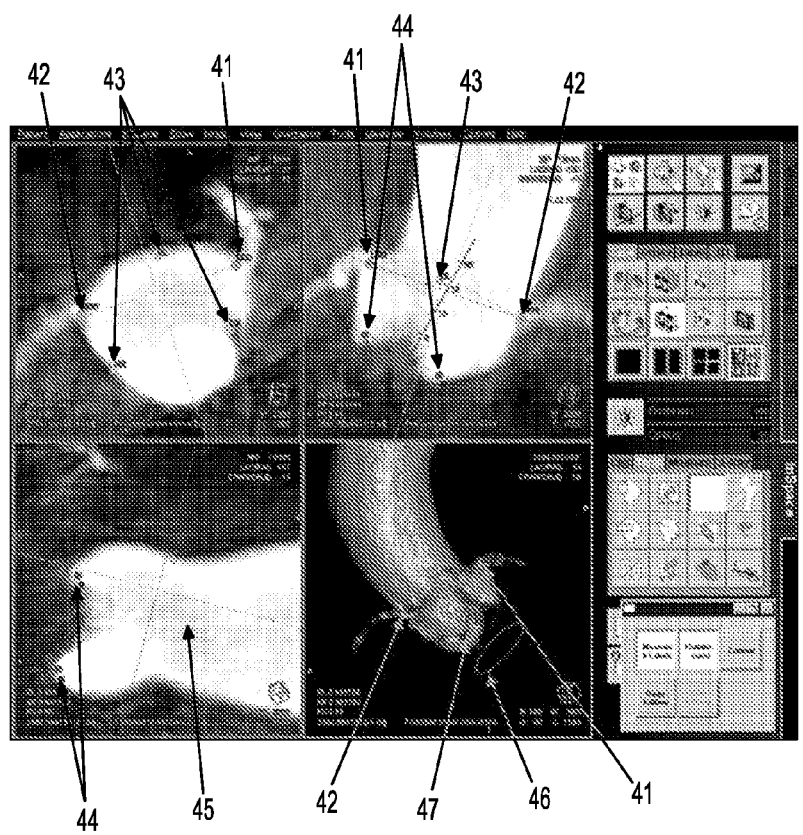
FIG. 4 illustrates a system display appearance after automatically visualizing the aortic root, according to an embodiment of the invention.

FIG. 4 illustrates a system display appearance after automatically performing the above steps to visualize the aortic root. Detected landmarks, including the left coronary ostium 41, the right coronary ostium 42, the commissures 43, the lowest cusp points 44, the centerline 45 and derived structures, such as the perpendicularity circle 46 and ruler 47 are shown in a 3D volume rendering and three orthogonal intersection planes with 15 mm slice thickness. The panel in the lower right shows a user interface added to an existing system.

After the results are presented, the physician can adjust landmarks and visualization if necessary. All of the interactions described above can be performed at an operating table using a joystick or other device provided with an angiography C-arm system.

By drag and drop, a user can edit the detected landmarks in the MPR screens and the volume rendering screen. Undo and redo functionality can ensure that editing mistakes can be easily corrected. Structures derived from the landmarks, such as the ruler, centerline and perpendicularity circle can be adapted in real-time.

Because the simultaneous display of too many structures can confuse a user, the display of some of the structures can be toggled on and off. A system according to an to embodiment of the invention can be configured in such a way that a preferred set of structures can be initially shown.

If landmark positions and visualization are satisfactory, a physician can perform the following steps.

Rotating the 3D Volume to an Appropriate C-Arm Angulation

Every rotation of the volume rendering view corresponds to a C-arm angulation, up to in-plane rotation. Therefore, using the displayed perpendicularity circle, a physician can virtually choose a volume rendering view that corresponds to appropriate C-arm angulation, and the C-arm will be automatically rotated to that angulation.

Switching the Contour View

When overlaying the 3D volume onto a live fluoroscopic scene, a contour view of the aortic root is presented which shows only the essential information needed for the prosthesis positioning and deployment steps. Therefore, less fluoroscopic image space is covered as compared to volume rendering, which improves fluoroscopic image quality in the overlay for a safer implantation.

For contour rendering, an efficient edge detection algorithm was implemented that includes four steps. First, the volume rendered aortic root image is segmented by thresholding the image intensity. The border pixels are detected as those that have at least one neighboring pixel that belongs to the background. Second, the gradients of the foreground pixels are calculated, and the gradients of the border pixels previously detected are given a maximum value, to create a gradient map. Third, edge pixels are detected on the gradient map by a hysteresis thresholding step, similar to a Canny edge detector, with the low and high threshold determined as a given percentage of the gradient map. Finally, the detected edge pixels are pruned by removing those connected components whose size is smaller than a predetermined number of pixels.

Overlaying Visualized 3D Structures onto Fluoroscopic Images

To overlay the rendered 3D visualization onto fluoroscopic images in real-time, software available with the angiographic C-arm system may be used. The 3D volume is inherently registered to the fluoroscopic images because both images are acquired on the same system. The overlay dynamically adapts to the position of the X-ray detector, to C-arm rotations and table movements, and can be used to adjust or fine-tune the C-arm angulation needed for implantation. The overlay does not compensate for patient and heart motions, but can be manually corrected in these cases.

Evaluation

A system and method according to an embodiment of the invention was evaluated on a group of patients who received an Edwards Sapien valve (Edwards Lifesiences, Irvine, USA) implanted as their first prosthesis. Twenty cases were analyzed where the overlay image scene was documented.

A first test was to determine how well a system according to an embodiment of the invention would have predicted an optimum perpendicular view. For each patient, the C-arm angulation that was actually chosen by the physician for implantation was identified. The deviation angle A of this angulation was compared with the perpendicular angulations suggested by a system according to an embodiment of the invention. If the physician would have used an angulation suggested by a system according to an embodiment of the invention, A would have been 0 degrees, otherwise A would be larger. In addition, the tilting angle B of the implanted prosthesis in the image under the chosen angulation was determined. The second value B indicates how perpendicular the valve prosthesis was right after implantation. The ellipsoid semi-major- and semi-minor-diameters of the upper prosthesis ring in the image in pixels were measured, and the degree of perpendicularity was determined from B=90−a cos (diam$_{minor}$/diam$_{major}$). The absolute difference of A and B indicates how well a system according to an embodiment of the invention could predict the tilting of the prosthesis. For the 20 evaluated patients, A is 2.0°±1.7° (mean±standard deviation), B is 5.7°±5.2°, and the absolute difference of A and B is 4.4°±3.8°.

A second test evaluated the accuracy of the overlay of the 3D image and the X-ray images. According to an embodiment of the invention, it may be assumed that the misalignment corresponds to a shift parallel to the projection plane, which simplifies evaluation but ignores rotations and zooming. For each patient, an image was acquired from the recorded overlay scene that showed a contrast injection under rapid pacing right before deployment of the prosthesis. The shift error was then measured as the distance (in pixels) of a landmark point that could be identified in the X-ray image and the 3D overlay, such as a lowest cusp point or a coronary ostium. Furthermore, the shift along the aortic root centerline was measured, which is the most important direction for guidance of implantation. Because of the projective geometry of the images, the measurement in pixels should be scaled using the known length of an object that is approximately the same distance from the X-ray detector. Thus, the results were scaled by the known height of the implanted prosthesis (in mm) divided by its measured height (in pixels). For the 20 evaluated patients, there was a shift error of 2.6 mm±1.6 mm (mean+standard deviation) and in centerline direction a shift error of 1.6 mm±1.2 mm.

Figure 5:
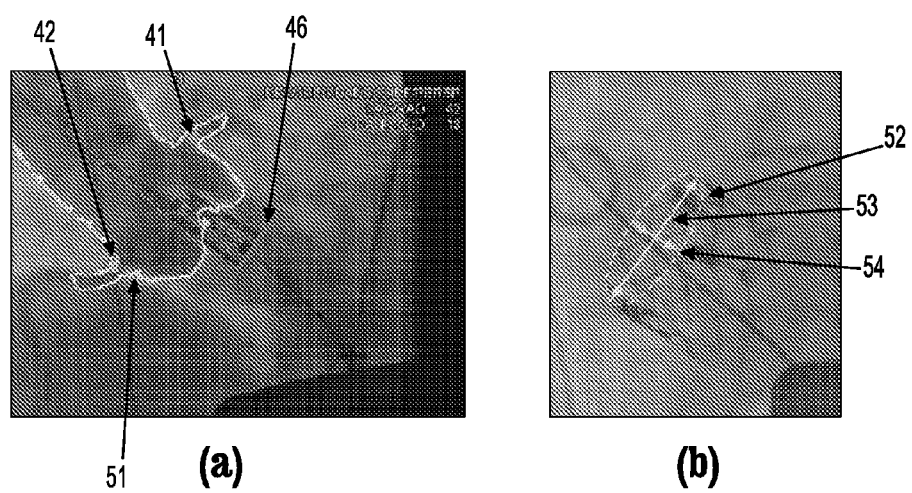
FIGS. 5(a)-(b) show a perfectly matching overlay and a measurement of a potential tilting of the prosthesis, according to an embodiment of the invention.

FIG. 5(a) shows a perfectly matching overlay 51 in which the measured misalignment is 0 mm. The left 41 and right 42 coronary ostia and the perpendicularity circle 46, viewed from the side, are also visible in the image. FIG. 5(b) shows a measurement of an ellipsoid 52 with semi-major axis 53 and semi-minor axis 54, to determine a potential tilting of the prosthesis. For clarity, an image from an angulation not used for valve deployment is shown.

The clinical evaluation indicates that a system according to an embodiment of the invention can make good predictions of the optimum C-arm angulation for prosthesis deployment. Reasons for suboptimal angulation estimation in some cases might be C-arm CT image artifacts and misdetections that result from asymmetric positioning of the injection pigtail catheter in the aortic root and from severe aortic regurgitation. The reported accuracy of the 3D overlay is only valid under repeat rapid pacing, which recovers the heart position during the 3D imaging and which minimizes heart motion. The reasons for pronounced deviation in a few patients could be dislocation of the aortic root by sheath-manipulation and accidental movements of the patients caused by the physicians.

System Implementations

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 6:
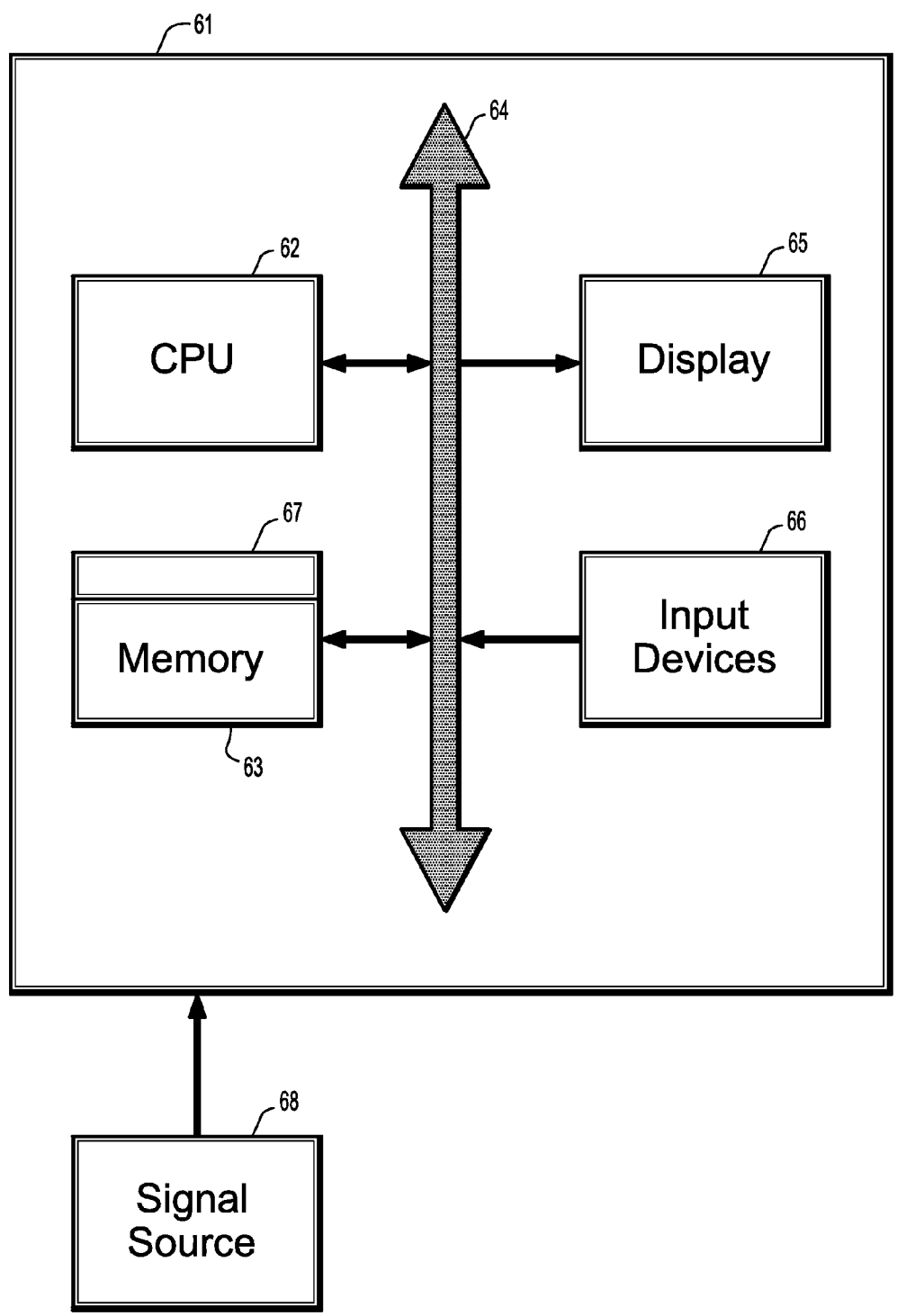
FIG. 6 is a block diagram of an exemplary computer system for implementing a method for guiding transcatheter aortic valve implantations based on interventional C-arm CT imaging, according to an embodiment of the invention.

FIG. 6 is a block diagram of an exemplary computer system for implementing a method for guiding transcatheter aortic valve implantations based on interventional C-arm CT imaging, according to an embodiment of the invention. Referring now to FIG. 6, a computer system 61 for implementing the present invention can comprise, inter alia, a central processing unit (CPU) 62, a memory 63 and an input/output (I/O) interface 64. The computer system 61 is generally coupled through the I/O interface 64 to a display 65 and various input devices 66 such as a mouse and a keyboard. The support circuits can include circuits such as cache, power supplies, clock circuits, and a communication bus. The memory 63 can include random access memory (RAM), read only memory (ROM), disk drive, tape drive, etc., or a combinations thereof. The present invention can be implemented as a routine 67 that is stored in memory 63 and executed by the CPU 62 to process the signal from the signal source 68. As such, the computer system 61 is a general purpose computer system that becomes a specific purpose computer system when executing the routine 67 of the present invention.

The computer system 61 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A computer implemented method for guiding transcatheter aortic valve implantations, the method implemented by the computer comprising the steps of:
   receiving an interventional 3D image of an aortic root reconstructed from a sequence of 2D images acquired from a C-arm computed tomography (CT) system being rotated about a patient through a predetermined number of degrees;
   segmenting the aortic root and detecting aortic root landmarks in the 3D image, wherein said aortic root landmarks include three lowest points of aortic root cusps, two coronary artery ostia, and three commissures points where the cusps meet;
   cropping an area inside the segmented aortic root out of the 3D volume for volume rendering;
   centering the 3D image on an intersection of two orthogonal planes, each containing the two detected coronary ostia, that are orthogonal to a plane spanned by three lowest points of the aortic root cusps; and
   volume rendering the 3D cropped aortic root image together with the detected landmarks onto a 2D image.

2. The method of claim 1, further comprising displaying said 2D volume rendering together with three orthogonal multi-planar reformatted (MPR) intersection planes.

3. The method of claim 2, wherein landmarks in the volume rendering window are rendered on top of the volume, the perpendicularity circle is displayed in the 3D volume window and the ruler is displayed in one of the intersection planes.

4. The method of claim 2, wherein the intersection planes are shown as maximum intensity projections (MIP) with a small thickness.

5. The method of claim 2, further comprising deriving a perpendicularity circle parallel to a plane spanned by three lowest points of the aortic root cusps and a ruler orthogonal to that plane, wherein said perpendicularity circle is displayed in the 3D volume rendering, and the ruler is displayed in one of the intersection planes.

6. The method of claim 1, wherein segmenting the aortic root and detecting aortic root landmarks in the 3D image comprises:
estimating a position, orientation, and scale of the aortic root to estimate a pose of said aortic root;
calculating a mean aortic root shape from a training set;
aligning said mean aortic root shape with the estimated pose of said aortic root; and
refining a boundary of said aortic root using a learning-based 3D boundary detector.

7. The method of claim 6, wherein a hierarchical approach is used that first detects a global object having all eight valve landmarks, uses the position, orientation, and scale of this global object to infer the rough position of individual landmarks, and refines each landmark in a small region under the guidance of its own specific landmark detector.

8. The method of claim 7, wherein the hierarchical approach comprises a marginal space learning (MSL) algorithm.

9. The method of claim 1, further comprising dilating the cropped aortic root shape, and adding a ball shape around each detected coronary ostia when cropping the aortic root shape from the 3D image.

10. The method of claim 1, further comprising calculating parameters for optimal values of a window center and a window width for a volume rendering transfer function by calculating $$c_{opt} = f_{c,in} \times m_{in} + f_{c,out} \times m_{out} + c_{offset},$$

$$w_{opt} = f_{w,in} \times m_{in} + f_{w,out} \times m_{out} + w_{offset},$$

wherein $m_{out}$ is the mean intensity of all voxels outside the boundary of the segmented aortic root with a distance less than n voxels to the boundary, $m_{in}$ is the mean intensity of all voxels inside the boundary of the segmented aortic root with a distance less than n voxels to the boundary, $f_{c,in}$ is a coefficient for $m_{in}$ for the optimal value of the window center, $f_{c,out}$ is a coefficient for $m_{out}$ for the optimal value of the window center, $f_{w,in}$ is a coefficient for $m_{in}$ for the optimal value of the window width, and $f_{w,out}$ is a coefficient for $m_{out}$ for the optimal value of the window width, $c_{offset}$ is a center offset and $w_{offset}$ is a width offset.

11. The method of claim 10, further comprising manually adjusting the optimal window width and window center values for the transfer function window for each of a set of training images, associating a definition of $c_{opt}$ and $w_{opt}$ with each training image, determining a value of $m_{in}$ and $m_{out}$ for each training image, and solving for the parameters $f_{c,in}$, $f_{c,out}$, $f_{w,in}$, $f_{w,out}$ in said set of equations using a least squares fit.

12. The method of claim 10, further comprising applying dilation and erosion operators on a binary segmentation mask of the aortic root to isolate those voxels within a predetermined distance from the aortic root boundary, wherein only those voxels outside and inside the aortic root boundary that are found by the dilation and erosion operations are used to calculate said optimized transfer function window parameters.

13. The method of claim 1, further comprising overlaying the volume rendering on a 2D live fluoroscopic image to display the cropped aortic root volume together with the detected landmarks, and presenting a contour view of the aortic root that displays information needed for a prosthesis positioning and deployment.

14. The method of claim 13, wherein rendering the contour comprises:
segmenting the volume rendered aortic root image by thresholding the image intensity, wherein border voxels are detected as those having at least one neighboring voxel that belongs to a background;
calculating gradients of foreground voxels are calculated, and assigning gradients of the border voxels a maximum value, to create a gradient map;
detecting edge voxels on the gradient map by a hysteresis thresholding step, with a low and high threshold determined as a given percentage of the gradient map; and
pruning the detected edge voxels by removing connected components whose size is smaller than a predetermined number of voxels.

15. A computer implemented method for guiding transcatheter aortic valve implantations, the method implemented by the computer comprising the steps of:
receiving an interventional 3D image of an aortic root reconstructed from a sequence of 2D images acquired from a C-arm computed tomography (CT) system being rotated about a patient through a predetermined number of degrees;
segmenting the aortic root and detecting aortic root landmarks in the 3D image, wherein said aortic root landmarks include three lowest points of aortic root cusps, two coronary artery ostia, and three commissures points where the cusps meet;
calculating parameters for optimal values of a window center and a window width for a volume rendering transfer function by calculating $$c_{opt} = f_{c,in} \times m_{in} + f_{c,out} \times m_{out} + c_{offset},$$

$$w_{opt} = f_{w,in} \times m_{in} + f_{w,out} \times m_{out} + w_{offset},$$

wherein $m_{out}$ is the mean intensity of all voxels outside the boundary of the segmented aortic root with a distance less than n voxels to the boundary, $m_{in}$ is the mean intensity of all voxels inside the boundary of the segmented aortic root with a distance less than n voxels to the boundary, $f_{c,in}$ is a coefficient for $m_{in}$ for the optimal value of the window center, $f_{c,out}$ is a coefficient for $m_{out}$ for the optimal value of the window center, $f_{w,in}$ is a coefficient for $m_{in}$ for the optimal value of the window width, and $f_{w,out}$ is a coefficient for $m_{out}$ for the optimal value of the window width, $c_{offset}$ is a center offset and $w_{offset}$ is a width offset;
volume rendering the 3D cropped aortic root image together with the detected landmarks onto a 2D image; and
overlaying the volume rendering on a 2D live fluoroscopic image to display the cropped aortic root volume together with the detected landmarks, and presenting a contour view of the aortic root that displays information needed for a prosthesis positioning and deployment.

16. The method of claim 15, further comprising:
cropping an area inside the segmented aortic root out of the 3D volume for volume rendering;
dilating the cropped aortic root shape; and
adding a ball shape around each detected coronary ostia when cropping the aortic root shape from the 3D image.

17. The method of claim 15, further comprising:
centering the 3D image on an intersection of two orthogonal planes, each containing the two detected coronary ostia, that are orthogonal to a plane spanned by three lowest points of the aortic root cusps.

18. The method of claim 15, further comprising deriving a perpendicularity circle parallel to a plane spanned by three lowest points of the aortic root cusps and a ruler orthogonal to that plane, and displaying said 2D volume rendering together with three orthogonal multi-planar reformatted (MPR) intersection planes, wherein said perpendicularity circle is displayed in the 3D volume rendering, and the ruler is displayed in one of the intersection planes.

19. A non-transitory program storage device readable by a computer, tangibly embodying a program of instructions executable by the computer to perform the method steps for guiding transcatheter aortic valve implantations, the method implemented by the computer comprising the steps of:
receiving an interventional 3D image of an aortic root reconstructed from a sequence of 2D images acquired from a C-arm computed tomography (CT) system being rotated about a patient through a predetermined number of degrees;
segmenting the aortic root and detecting aortic root landmarks in the 3D image, wherein said aortic root landmarks include three lowest points of aortic root cusps, two coronary artery ostia, and three commissures points where the cusps meet;
cropping an area inside the segmented aortic root out of the 3D volume for volume rendering;
centering the 3D image on an intersection of two orthogonal planes, each containing the two detected coronary ostia, that are orthogonal to a plane spanned by three lowest points of the aortic root cusps; and
volume rendering the 3D cropped aortic root image together with the detected landmarks onto a 2D image.

20. The computer readable program storage device of claim 19, the method further comprising displaying said 2D volume rendering together with three orthogonal multi-planar reformatted (MPR) intersection planes.

21. The computer readable program storage device of claim 20, wherein landmarks in the volume rendering window are rendered on top of the volume, the perpendicularity circle is displayed in the 3D volume window and the ruler is displayed in one of the intersection planes.

22. The computer readable program storage device of claim 20, wherein the intersection planes are shown as maximum intensity projections (MIP) with a small thickness.

23. The computer readable program storage device of claim 20, the method further comprising deriving a perpendicularity circle parallel to a plane spanned by three lowest points of the aortic root cusps and a ruler orthogonal to that plane, wherein said perpendicularity circle is displayed in the 3D volume rendering, and the ruler is displayed in one of the intersection planes.

24. The computer readable program storage device of claim 19, wherein segmenting the aortic root and detecting aortic root landmarks in the 3D image comprises:
estimating a position, orientation, and scale of the aortic root to estimate a pose of said aortic root;
calculating a mean aortic root shape from a training set;
aligning said mean aortic root shape with the estimated pose of said aortic root; and
refining a boundary of said aortic root using a learning-based 3D boundary detector.

25. The computer readable program storage device of claim 24, wherein a hierarchical approach is used that first detects a global object having all eight valve landmarks, uses the position, orientation, and scale of this global object to infer the rough position of individual landmarks, and refines each landmark in a small region under the guidance of its own specific landmark detector.

26. The computer readable program storage device of claim 25, wherein the hierarchical approach comprises a marginal space learning (MSL) algorithm.

27. The computer readable program storage device of claim 19, the method further comprising dilating the cropped aortic root shape, and adding a ball shape around each detected coronary ostia when cropping the aortic root shape from the 3D image.

28. The computer readable program storage device of claim 19, the method further comprising calculating parameters for optimal values of a window center and a window width for a volume rendering transfer function by calculating $$c_{opt} = f_{c,in} \times m_{in} + f_{c,out} \times m_{out} + c_{offset},$$

$$w_{opt} = f_{w,in} \times m_{in} + f_{w,out} \times m_{out} + w_{offset},$$

wherein $m_{out}$ is the mean intensity of all voxels outside the boundary of the segmented aortic root with a distance less than n voxels to the boundary, $m_{in}$ is the mean intensity of all voxels inside the boundary of the segmented aortic root with a distance less than n voxels to the boundary, $f_{c,in}$ is a coefficient for $m_{in}$ for the optimal value of the window center, $f_{c,out}$ is a coefficient for $m_{out}$ for the optimal value of the window center, $f_{w,in}$ is a coefficient for $m_{in}$ for the optimal value of the window width, and $f_{w,out}$ is a coefficient for $m_{out}$ for the optimal value of the window width.

29. The computer readable program storage device of claim 28, the method further comprising manually adjusting the optimal window width and window center values for the transfer function window for each of a set of training images, associating a definition of $c_{opt}$ and $w_{opt}$ with each training image, determining a value of $m_{in}$ and $m_{out}$ for each training image, and solving for the parameters $f_{c,in}$, $f_{c,out}$, $f_{w,in}$, $f_{w,out}$ in said set of equations using a least squares fit.

30. The computer readable program storage device of claim 28, the method further comprising applying dilation and erosion operators on a binary segmentation mask of the aortic root to isolate those voxels within a predetermined distance from the aortic root boundary, wherein only those voxels outside and inside the aortic root boundary that are found by the dilation and erosion operations are used to calculate said optimized transfer function window parameters.

31. The computer readable program storage device of claim 19, the method further comprising overlaying the volume rendering on a 2D live fluoroscopic image to display the cropped aortic root volume together with the detected landmarks, and presenting a contour view of the aortic root that displays information needed for a prosthesis positioning and deployment.

32. The computer readable program storage device of claim 31, wherein rendering the contour comprises:
segmenting the volume rendered aortic root image by thresholding the image intensity, wherein border voxels are detected as those having at least one neighboring voxel that belongs to a background;
calculating gradients of foreground voxels are calculated, and assigning gradients of the border voxels a maximum value, to create a gradient map;
detecting edge voxels on the gradient map by a hysteresis thresholding step, with a low and high threshold determined as a given percentage of the gradient map; and pruning the detected edge voxels by removing connected components whose size is smaller than a predetermined number of voxels.

* * * * *